United States Patent
Jin

(10) Patent No.: US 9,403,748 B2
(45) Date of Patent: Aug. 2, 2016

(54) SYNTHESIS OF SHORT CHAIN CARBOXYLIC ACIDS FROM CARBOHYDRATE BIOMASS

(71) Applicant: EMPIRE TECHNOLOGY DEVELOPMENT LLC, Wilmington, DE (US)

(72) Inventor: Fangming Jin, Shanghai (CN)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/652,203

(22) PCT Filed: Dec. 14, 2012

(86) PCT No.: PCT/CN2012/086666
§ 371 (c)(1),
(2) Date: Jun. 15, 2015

(87) PCT Pub. No.: WO2014/089827
PCT Pub. Date: Jun. 19, 2014

(65) Prior Publication Data
US 2015/0321988 A1    Nov. 12, 2015

(51) Int. Cl.
*C07C 51/00*    (2006.01)

(52) U.S. Cl.
CPC ..................... *C07C 51/00* (2013.01)

(58) Field of Classification Search
CPC ........................................ C07C 51/00
USPC ................................ 562/513, 515
See application file for complete search history.

(56) References Cited

FOREIGN PATENT DOCUMENTS

EP              0523014 A2 *   1/1993
WO     WO2014/089827 A1        6/2014

OTHER PUBLICATIONS

Niemela et al. The Conversion of Cellulose into Carboxylic Acids by a Drastic Alkali Treatment. Biomass, vol. 11, 1986, 215-221.*

International Search Report and Written Opinion for International Application No. PCT/CN2012/086666 mailed Sep. 19, 2013.
Jin et al., Hydrothermal Conversion of Biomass into Value-Added Products: Technology That Mimics Nature, *Bioresources* (2009), 4(2):704-713.
Jin et al., Controlling Hydrothermal Reaction Pathways to Improve Acetic Acid Production From Carbohydrate Biomass, *Environ. Sci. Technol.* (2005), 39(6):1893-1902.
Kong et al., Technical Note Hydrothermal Catalytic Conversion of Biomass for Lactic Acid Production, *Journal of Chemical Technology and Biotechnology* (Nov. 22, 2007), 83:383-388.
Blahu et al., Simulation of a hybrid fermentation-separation process for production of butyric acid, Chemical Papers, 64(2) pp. 213-222 (2010).
Feng et al., Green and economical production of propionic acid by Propionibacterium freudenreichii CCTCC M207015 in plant fibrous-bed bioreactor, Bioresource Technology, 102(10) pp. 6141-6146 (May 2011).
Jiang et al., Butyric acid fermentation in a fibrous bed bioreactor with immobilized Clostridium tyrobutyricum from cane molasses, Bioresource Technology, 100(13) pp. 3403-3409 (Jul. 2009).
Li et al., Continuous butyric acid production by corn stalk immobilized Clostridium thermobutyricum cells, African Journal of Microbiology Research 5(6) pp. 661-666 (Mar. 18, 2011).
Liu et al., Glycerol/glucose co-fermentation: one more proficient process to produce propionic acid by Propionibacterium acidipropionici, Current Microbiology, 62(1) pp. 152-158 (Jan. 2011).
Song et al., Butyric acid production from brown algae using Clostridium tyrobutyricum ATCC 25755, Biotechnology and Bioprocess Engineering, 16(1) pp. 42-49 (Feb. 2011).
Zhang, Propionic acid production from glycerol by metabolically engineered Propionibacterium acidipropionici, Process Biochemistry, 44(12) pp. 1346-1351 (Dec. 2009).
Zhang et al., Optimization of medium composition for butyric acid production by Clostridium thermobutyricum using response surface methodology, Bioresource Technology, 100(18) pp. 4284-4288 (Sep. 2009).

* cited by examiner

*Primary Examiner* — Sikarl Witherspoon
(74) *Attorney, Agent, or Firm* — Pepper Hamilton LLP

(57) ABSTRACT

The current disclosure provides methods for producing C2-C5 carboxylic acids from a carbohydrate source. In some embodiments, the method may be: (a) contacting the carbohydrate source with an alkali to form a plurality of intermediate compounds; and (b) reducing the intermediate compounds to form at least one C2-C5 carboxylic acid. In some embodiments, the carbohydrate source may be organic waste.

22 Claims, 3 Drawing Sheets

SYNTHESIS OF SHORT CHAIN CARBOXYLIC ACIDS FROM CARBOHYDRATE BIOMASS

CLAIM OF PRIORITY

This application is a U.S. national stage filing under 35 U.S.C. §371 of International Application No. PCT/CN2012/086666 filed on Dec. 14, 2012 entitled "SYNTHESIS OF SHORT CHAIN CARBOXYLIC ACIDS FROM CARBOHYDRATE BIOMASS," which is incorporated herein by reference in its entirety.

BACKGROUND

Short chain carboxylic acids of C2 to C5 carbon atoms in length have a wide range of applications, including from serving as monomers for polymers, paints, and coatings, to fragrance sources for perfumes and other commodities. Currently, such carboxylic acids are produced mainly from petrochemical sources. For example, propionic acid, which is routinely used in making preservatives and polymers, is produced by carbonylation of ethylene. Similarly, acetic acid is produced by carbonylation of methanol or by oxidation of ethylene. Thus, the production of short chain carboxylic acids depends heavily on the petrochemical industry and may become limited in near future due to the depletion of fossil fuels. Further, the production of carboxylic acids from such sources may also lead to other serious issues, such as environmental pollution and global warming, as a result of excess $CO_2$ emissions.

Alternative methods for producing carboxylic acids in industry include fermentation by microorganisms and hydrothermal oxidation. For example, the fermentation of glycerol and other carbohydrate biomass leads to the production of propionic acid. Certain microorganisms such as *C. Tyrobutyricum* produce butyric acid as an end-product by fermentation, with acetic acid as a minor by-product. However, the efficiency of such processes is low and is highly dependent on the type and the quality of raw biomass used. Although there have been reports on the production of acetic acid from hydrothermal oxidation of carbohydrates, the yield of acetic acid is minimal and needs to be enhanced. Thus, there remains a need to identify alternative sources for producing these carboxylic acids, and developing methods for producing short chain carboxylic acids from carbohydrate biomass with high efficiency is desirable.

SUMMARY

The current disclosure provides methods for producing C2-C5 carboxylic acids from a carbohydrate source. In one embodiment, the method may include: (a) contacting the carbohydrate source with an alkali to form a plurality of intermediate compounds; and (b) reducing the intermediate compounds to form at least one C2-C5 carboxylic acid.

In another embodiment, a method for treating organic waste may include: (a) contacting the organic waste with an alkali to form a plurality of intermediate compounds; and (b) reducing the intermediate compounds to form at least one C2-C5 carboxylic acid.

DETAILED DESCRIPTION

Figure 1:
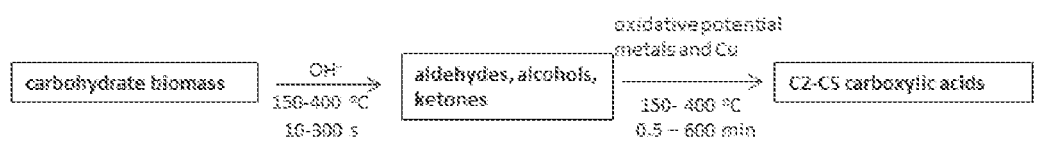
FIG. 1 depicts a flow diagram of converting a carbohydrate mass to carboxylic acids according to an embodiment.

This disclosure is not limited to the particular systems, devices and methods described, as these may vary. The terminology used in the description is for the purpose of describing the particular versions or embodiments only, and is not intended to limit the scope.

The rapid depletion of fossil fuels has been a driving force to identify alternative sources for the production of short chain carboxylic acids. Carbohydrate biomass materials provide one such source for the production of such acids. Carbohydrate biomass materials are carbon, hydrogen and oxygen based, and encompass a wide variety of materials including plants, wood, garbage, paper, crops and waste products. Carbohydrate sources may also include some waste materials, such as forest residues, municipal solid wastes, waste paper and crop residues. The main components of biomass materials are cellulose, starch and hemi-cellulose, with cellulose being about 36-42% of dry weight of non-food biomass feedstock, and hemicellulose being about 21-25% of dry weight of non-food biomass feedstock. Cellulose consists of a linear chain of several hundred to over ten thousand $\beta(1\rightarrow4)$ linked D-glucose units. Cellulose is the structural component of the primary cell wall of green plants and many forms of algae, making it one of the most common organic compounds on Earth. Starch is similar to cellulose and contains a large number of glucose units joined by $\alpha(1\rightarrow4)$ linkages. Starch is produced by all green plants as an energy store and thus is the most common carbohydrate in the human diet. Hemicellulose is formed from both 6-carbon (C6) sugars and 5-carbon (C5) sugars. Hemicellulose monomers may include glucuronic acid, galactose, mannose, rhamnose, arabinose, most of the D-pentose sugars and small amounts of L-sugars, with xylose being present in the largest amount.

Biomass materials may be broken down into simple sugars, which may later be converted into organic acids by various methods. Although traditional biochemical processes, such as fermentation, can convert biomass to short chain carboxylic acids, their reaction rate is generally slow. Further, cellulose and hemicellulose in lignocellulosic materials cannot be used directly for bioconversion because of the intimate association with lignin. In addition, specific pretreatment processes may be involved to separate the carbohydrates from lignin.

Organic waste serves as a good economical source for producing short chain carboxylic acids. The use of organic waste as a source for carboxylic acid production may also alleviate another global problem. The safe disposal of organic waste or contaminating materials has been recognized as a significant health and economic issue for many years. The ability to merely dump raw materials into the oceans or landfills is no longer a favored mechanism for disposal. Not only do landfills face a limitation on space and require significant energy to transport and deposit materials, but they are recognized as potential health hazards and ecologically destructive of their locations and adjacent land areas, especially because of underground seepage of materials. Thus, methods to reduce organic waste dump by converting them to economical products are becoming increasingly important.

"Biomass" means any organic, non-fossil material that is derived from the mass of any biological organism excluding mass that has been transformed by geological processes in substances such as coal or petroleum.

The present disclosure provides methods to produce C2 to C5 carboxylic acids from a carbohydrate source, such as biomass. In some embodiments, a starting carbohydrate material may be hydrolyzed to form intermediate compounds. The intermediate compounds may be reduced to produce C2 to C5 carboxylic acids. The C2 to C5 carboxylic acids may be saturated or unsaturated carboxylic acids. The reaction does not include an oxidation step. The outline of the reaction is shown in FIG. 1. Examples of C2 to C5 carboxylic acids that may be obtained by such a reaction are acetic acid, lactic acid, propanoic acid, butanoic acid, isobutyric acid, pentanoic acid, 4-pentenoic acid, 5-hydroxy-3-pentenoic acid, γ-hydroxybutyric acid, 5-hydroxy pentanoic acid, 3-butenoic acid, 2-methyl butanoic acid, and combinations thereof.

In some embodiments, the carbohydrate source may be biomass or organic waste. Non-limiting examples of biomass or organic waste may include, food processing byproducts, vegetable mixtures, fruit mixtures, maize straw, wheat bran, rice hulls, glucose, grains, plant matter, animal products, beef suet, and the like. So as not to compete for food sources, short chain carboxylic acids may also be produced from the waste materials. Some examples of non-food biomass materials may include, but are not limited to, sawdust, corn stover, wheat straw, rice straw, switchgrass, cellulose, starch, bagasse, poplar wood, paper mill waste and municipal paper waste.

In some embodiments, the hydrolysis step may be carried out by heating the carbohydrate source in the presence of an alkali catalyst to a temperature of about 150° C. to about 400° C., about 200° C. to about 400° C., about 250° C. to about 400° C., about 300° C. to about 400° C., or about 350° C. to about 400° C. Specific examples include about 150° C., about 175° C., about 250° C., about 300° C., about 400° C., and ranges between any two of these values. The alkali catalyst may be an alkali metal compound, an alkali metal alkoxide, an alkali metal hydroxide, a carbonate, an alkali metal hydride, an alkali earth metal oxide, an alkali metal silicate, or a combination thereof. Although the carbohydrate hydrolysis may occur in the absence of an alkali catalyst, the presence of the alkali may result in improving the yield. Suitable alkali catalysts or combinations of alkali catalysts include NaOH, KOH, LiOH, $NH_4OH$, $NaOCH_3$, $KOCH_3$, $Na_2CO_3$, $K_2CO_3$, $Cs_2CO_3$, CaO, MgO, $Al(OH)_3$, $AlO(OH)_2$, $Na_2SiO_3$ and the like.

During hydrolysis, the heating of the carbohydrate source may be carried out for any suitable period of time. For example, heating may be performed for about 10 seconds to about 5 minutes, about 30 seconds to about 5 minutes, about 1 minute to about 5 minutes, or about 3 minutes to about 5 minutes. Specific examples include about 10 seconds, about 30 seconds, about 1 minute, about 2 minutes, about 3 minutes, about 4 minutes, about 5 minutes, and ranges between any two of these values. In some cases, longer periods of times may be used.

The hydrolysis of the carbohydrates, as performed by the steps described herein, may result in the generation of various intermediate compounds of C2 to C5 carbon atoms. By way of example, but not wishing to be bound by theory, during hydrolysis, the carbohydrates may undergo several changes, such as Lobry de Bruyn-Alberda van Ekenstein transformation, elimination of water molecule and benzilic acid rearrangement to generate a mixture of intermediate compounds.

The Lobry-de-Bruyn-Alberda-van-Ekenstein transformation is the base or acid catalyzed transformation of an aldose into the ketose isomer or vice versa, with a tautomeric enediol as reaction intermediate. By such transformations, for example, ketoses may be transformed into 3-ketoses. The benzilic acid rearrangement results in 1,2-diketones undergoing a rearrangement in the presence of a strong base to yield α-hydroxycarboxylic acids.

Figure 2:
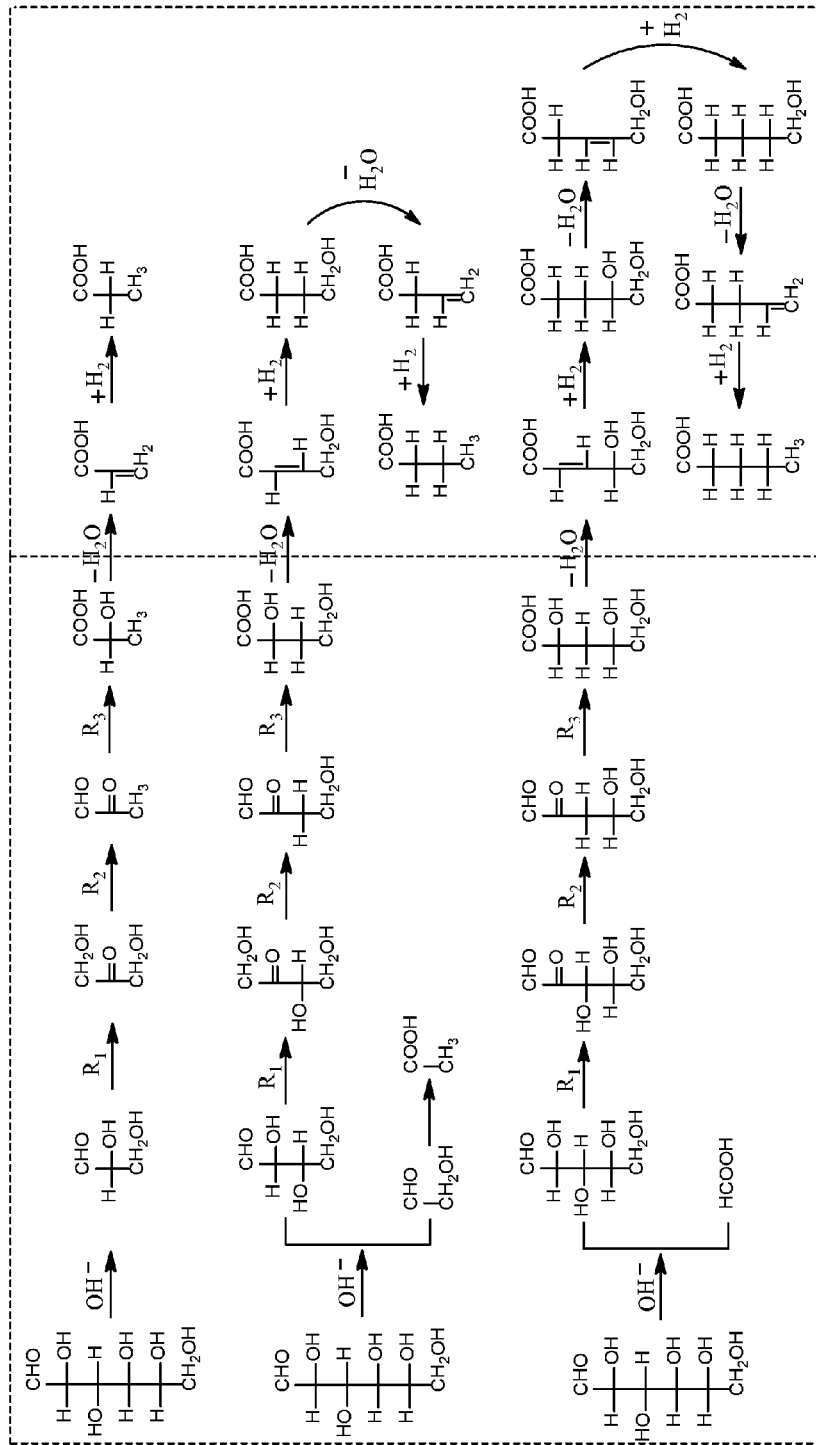
FIG. 2 depicts the reaction mechanisms involving conversion of glucose to C2-C5 carboxylic acids according to an embodiment.

An exemplary reaction mechanism of the hydrolysis step may be as follows. Hydrolysis of cellulose may result in the formation of glucose and other monomers. Glucose in turn may hydrolyze to glyceraldehyde. Glyceraldehyde may undergo Lobry de Bruyn-Alberda van Ekenstein transformation to form dihydroxy acetone. The subsequent elimination of water molecule may result in the formation of methyl glyoxal. Methyl glyoxal may undergo benzilic acid rearrangement to form lactic acid. FIG. 2 illustrates various reaction mechanisms, intermediates and the final carboxylic acids generated by these processes. The reaction mechanisms and intermediate compounds that are described herein are for the purposes of illustration only. In some embodiments, only some of the reaction mechanisms depicted may occur. In some embodiments, only some of the intermediate compounds may be generated.

The intermediate compounds generated as described herein may have various functional groups, such as hydroxyl groups, carboxyl groups, keto groups, and aldehyde groups. Examples of C2 and C3 intermediate compounds include, but are not limited to, acetic acid, glyceraldehyde, dihydroxy acetone, methyl glyoxal, lactic acid, acetaldehyde, and 2-hydroxy acetaldehyde. Examples of C4 intermediate compounds that may be generated are threose, erythrulose, 3-deoxy threosone, 3-deoxy tetranoic acid and the like. Non-limiting examples of C5 intermediate compounds include lyxose, D-xylosone, 3-deoxy pentosone, trihydroxypentanal and the like.

In some embodiments, before proceeding to the reduction step, the pH of the reaction mixture may be adjusted to a pH range, such as from about pH 2 to about pH 6, from about pH 3 to about pH 6, from about pH 4 to about pH 6, or from about pH 5 to about pH 6. Specific examples of the pH value include about pH 2, about pH 3, about pH 4.5, about pH 6, and ranges between any two of these values. The pH of the mixture may be adjusted by using any acid or combination of acids, such as $H_3PO_4$, HCl, $H_2SO_4$, $HClO_4$, $HNO_3$ and the like.

The reduction step may be carried out by heating the intermediate compounds in the presence of a mixture of metal catalysts, such as mixtures containing metals of high oxidative potential and copper. Examples of metals with high oxidative potential include Li, K, Ba, Ca, Na, Mg, Al, Mn, Zn, Cr and the like. In some embodiments, the metal catalyst mixture may be Li and Cu, K and Cu, Ca and Cu, Na and Cu, Mg and Cu, Al and Cu, Zn and Cu, and combinations thereof. In the reduction step, metals with high oxidative potential may function as a reductant to produce hydrogen from water, and Cu may activate hydrogen. In some embodiments, Ni, Pt, Ag, Au may be used in place of Cu.

In some embodiments, the reduction step may be carried out by heating the intermediate compounds in the presence of the metal catalyst mixture described herein to a temperature of about 150° C. to about 400° C., about 200° C. to about 400° C., about 250° C. to about 400° C., about 300° C. to about 400° C., or about 350° C. to about 400° C. Specific examples include about 150° C., about 175° C., about 250° C., about 300° C., about 400° C., and ranges between any two of these values. The heating step can generally be performed for any suitable period of time. Suitable time periods for this reaction process may include about 30 seconds to about 10 hours, about 1 minute to about 10 hours, about 10 minutes to about 10 hours, about 100 minutes to about 10 hours, about 200 minutes to about 10 hours, about 300 minutes to about 10 hours, or about 400 minutes to about 10 hours. Specific examples include about 30 seconds, about 1 minute, about 20 minutes, about 30 minutes, about 100 minutes, about 250 minutes, about 350 minutes, about 500 minutes, about 10 hours, and ranges between any two of these values. In some cases, longer periods of times may be used.

In some embodiments, the reduction step may be performed by any reduction process known in the art, such as performing the reaction in the presence of $H_2$ gas or formic acid.

The resulting product may contain a mixture of the following carboxylic acids: acetic acid, lactic acid, propanoic acid, butanoic acid, isobutyric acid, pentanoic acid, 4-pentenoic acid, 5-hydroxy-3-pentenoic acid, γ-hydroxybutyric acid, 5-hydroxy pentanoic acid, 3-butenoic acid, 2-methyl butanoic acid, and combinations thereof. In some embodiments, acetic acid is present in about 20 weight percent to about 40 weight percent of the total mixture; isobutyric acid may be present in about 10 weight percent to about 20 weight percent of the total mixture; propanoic acid may be present in about 25 weight percent to about 40 weight percent of the total mixture; butanoic acid may be present in about 5 weight percent to about 10 weight percent of the total mixture; 2-methyl butanoic acid may be present in about 5 weight percent to about 10 weight percent of the total mixture; and pentanoic acid may be present in about 15 weight percent to about 25 weight percent of the total mixture.

The process described herein may be performed in a batch reactor or in a continuous flow reactor. In the batch reactor, the substrate may be put in the reactor at the beginning of the degradation period after which the reactor is closed for the entire period without adding additional substrate. In the continuous flow reactor, the reactor may be filled continuously with fresh material and also emptied continuously.

Short chain carboxylic acids that are generated as described herein may be purified by any method known in the art. For example, the short chain carboxylic acids may be purified by using one or more methods including solvent extraction, distillation, and the like. Solvents such as a 40% aqueous solution of trimethylamine, hot water or aqueous NaOH may be used for extraction. The carboxylic acids may be further purified by distillation, electrodialysis, reverse-osmosis, supercritical $CO_2$ extraction or any other methods known in the art.

The process described herein may have many advantages over the methods known in the art. For example, cellulose may be directly converted to short chain carboxylic acids without any pretreatment, such as treating cellulose with enzymes prior to hydrolysis. In addition, the process described herein does not use any oxidants, such as oxygen or hydrogen peroxide. Further, the process does not require elaborately prepared catalysts, and the short chain carboxylic acid products may be obtained in a short reaction time period. Furthermore, the process does not generate any solid residue from carbohydrate biomass in the liquid after reactions.

EXAMPLES

Example 1

Two-Step Production of Short Chain Carboxylic Acids from Glucose

The experiments were conducted in a batch reactor system. In the first step, about 0.035 grams of glucose and 2 mL of 2.5 M NaOH were introduced into a batch reactor made of stainless steel tubing (9.5 millimeters wide, 1 millimeter wall thickness and 120 millimeters long) with two end fittings, providing an inner volume of 5.7 cm$^3$. After loading, the reactor was immersed in a salt bath preheated to a temperature of about 300° C. The reactor was incubated at this temperature for about 50 seconds with constant shaking. At the end of this reaction period, the reactor was taken out of the salt bath and immediately plunged into a cold water bath to quench the reaction. Before the commencement of the second step, the pH of the reaction mixture was adjusted to pH 2 by adding a few drops of $H_3PO_4$. About 12 millimoles of Cu and 4.35 millimoles of Al were added to the reaction mixture, and the reactor was further incubated in the salt bath preheated to 275° C. for 1 hour. At the end of the reaction period, the reactor was placed in a cold water bath to quench the reaction. The contents of the reaction mixture were analyzed by GC/MS.

Example 2

Product Analysis

Figure 3:
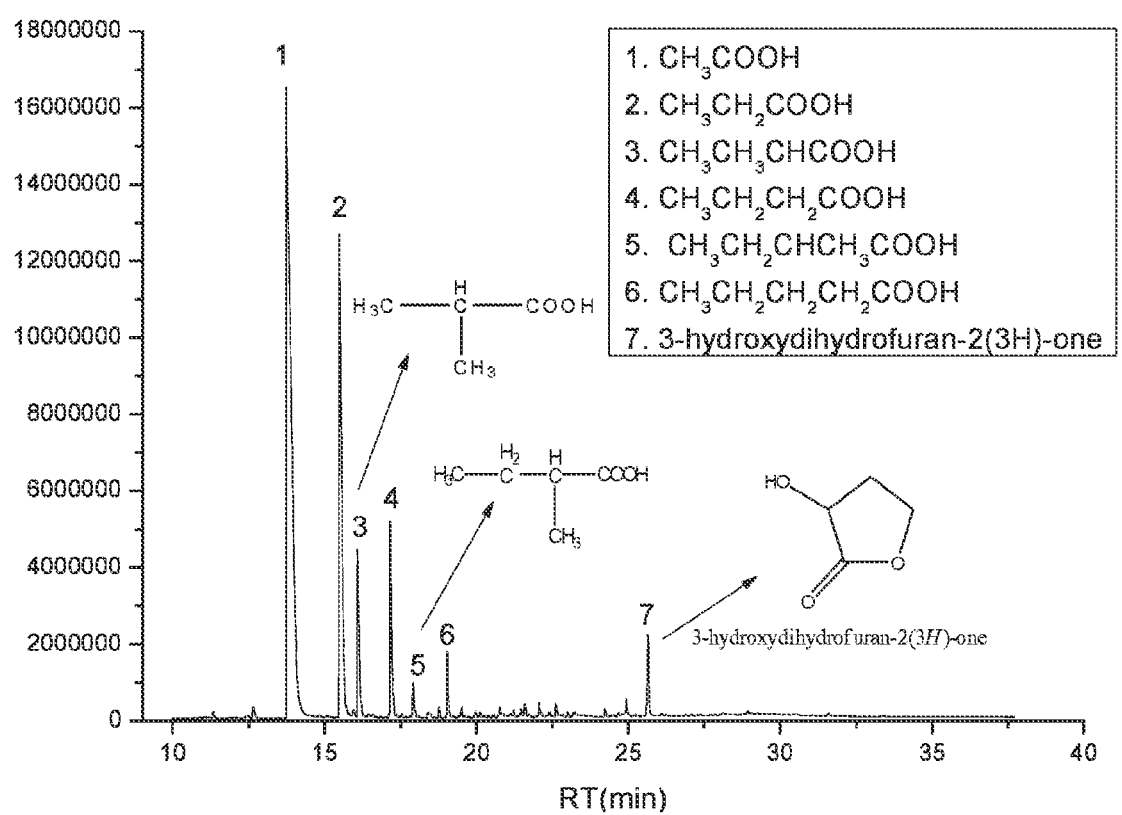
FIG. 3 shows a GC-MS chromatography of the product sample obtained after a two-step reaction according to an embodiment.

The samples obtained from the reaction of Example 1 were analyzed by GC/MS. For GC/MS analyses, a Hewlett-Packard model 5890 Series II gas chromatograph equipped with a model 5890B Mass Selective Detector was used. The samples were separated on a HP-INNOWAX capillary column (cross-linked polyethyleneglycol) for water-soluble compounds with polar functional groups (—OH, —C=O, —COOH), and using helium as the carrier. The obtained GC/MS chromatogram is depicted in FIG. 3. Peaks labeled 1-6 represent the compounds that were identified.

Example 3

Production of Short Chain Carboxylic Acids from Rice Hulls

The experiments are conducted in a batch reactor system. In the first step, about 5 grams of rice hull and 2 mL of 2.5 M NaOH are introduced into a batch reactor made of stainless steel tubing (10 millimeter wall thickness) with two end fittings, and having an inner volume of 50 cm$^3$. After loading, the reactor is immersed in a salt bath that is preheated to a temperature of about 300° C. The reactor is incubated at this temperature for about 50 seconds with constant shaking. At the end of this reaction period, the reactor is taken out of the salt bath and immediately plunged into a cold water bath to quench the reaction. Before starting the second step, the pH of the reaction mixture is adjusted to pH 3 by adding a few drops of $H_3PO_4$. About 12 micromoles of Cu and 5 micromoles of Al are added to the reaction mixture, and the reactor is further incubated in the salt bath preheated to 275° C. for 1 hour. At the end of the reaction period, the reactor is placed in a cold water bath to quench the reaction. The contents of the reaction mixture will be analyzed by GC/MS.

Example 4

Production of Short Chain Carboxylic Acids from Organic Waste

The experiments are conducted in a batch reactor system. In the first step, about 5 grams of organic waste (mixture of carrots, onions, potatoes and beef suet) and 2 mL of 2.5 M NaOH are introduced into a batch reactor made of stainless steel tubing (10 millimeter wall thickness) with two end fittings, and having an inner volume of 5.7 cm$^3$. After loading, the reactor is immersed in a salt bath that is preheated to a temperature of about 300° C. The reactor is incubated at this temperature for about 50 seconds with constant shaking. At the end of this reaction period, the reactor is taken out of the salt bath and immediately plunged into a cold water bath to quench the reaction. Before starting the second step, the pH of the reaction mixture is adjusted to pH 3 by adding a few drops of $H_3PO_4$. About 12 micromoles of Cu and 5 micromoles of Al are added to the reaction mixture, and the reactor is further incubated in the salt bath preheated to 275° C. for 1 hour. At the end of the reaction period, the reactor is placed in a cold water bath to quench the reaction. The contents of the reaction mixture will be analyzed by GC/MS.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of producing C2-C5 carboxylic acids from a carbohydrate source, the method comprising:
    contacting the carbohydrate source with an alkali to form a plurality of intermediate compounds; and
    reducing the intermediate compounds using a metal catalyst to form at least one C2-C5 carboxylic acid.

2. The method of claim 1, wherein contacting the carbohydrate source with the alkali comprises contacting the carbohydrate source selected from the group consisting of organic waste, food processing byproduct, a vegetable mixture, a fruit mixture, sawdust, maize straw, wheat bran, rice hulls, cellulose, starch, glucose, grains, plant matter, animal product, beef suet, and a combination thereof with the alkali.

3. The method of claim 1, wherein reducing the intermediate compounds comprises reducing the intermediate compounds to form the at least one C2-C5 carboxylic acid selected from the group consisting of acetic acid, lactic acid, propanoic acid, butanoic acid, isobutyric acid, pentanoic acid, 4-pentenoic acid, 5-hydroxy-3-pentenoic acid, γ-hydroxybutyric acid, 5-hydroxy pentanoic acid, 3-butenoic acid, 2-methyl butanoic acid, and a combination thereof.

4. The method of claim 1, wherein contacting the carbohydrate source with the alkali comprises contacting the carbohydrate source with the alkali to form the intermediate compound, wherein the intermediate compound is a carbohydrate having one or more of the following functional groups: a hydroxyl group, a carboxyl group, a keto group, and an aldehyde group.

5. The method of claim 1, wherein contacting the carbohydrate source with the alkali comprises contacting the carbohydrate source with the alkali selected from the group consisting of an alkali metal compound, an alkali metal, an alkoxide, an alkali metal hydroxide, a carbonate, an alkali metal hydride, and a combination thereof.

6. The method of claim 1, wherein the contacting comprises heating the carbohydrate source and the alkali to a temperature of about 150° C. to about 400° C. for about 10 seconds to about 5 minutes.

7. The method of claim 1, wherein the reducing further comprises adjusting the pH of a reaction mixture to about pH 2 to about pH 6.

8. The method of claim 1, wherein the reducing comprises heating the intermediate compounds and a metal catalyst mixture to a temperature of about 150° C. to about 400° C. for about 30 seconds to about 10 hours, wherein the metal catalyst mixture comprises a mixture of metal having high oxidation potential and copper.

9. The method of claim 1, wherein the method is performed in a batch reactor or a continuous flow reactor.

10. A method for treating organic waste, the method comprising:
    contacting the organic waste with an alkali to form a plurality of intermediate compounds; and
    reducing the intermediate compounds using a metal catalyst to form at least one C2-C5 carboxylic acid.

11. The method of claim 10, wherein contacting the organic waste with the alkali comprises contacting the organic waste selected from the group consisting of food processing byproduct, a vegetable mixture, a fruit mixture, sawdust, rice hulls, cellulose, starch, glucose, grains, plant matter, animal product, beef suet, and a combination thereof with the alkali.

12. The method of claim 10, wherein reducing the intermediate compounds comprises reducing the intermediate compounds to form the at least one C2-C5 carboxylic acid selected from the group consisting of acetic acid, lactic acid, propanoic acid, butanoic acid, isobutyric acid, pentanoic acid, 4-pentenoic acid, 5-hydroxy-3-pentenoic acid, γ-hydroxybutyric acid, 5-hydroxy pentanoic acid, 3-butenoic acid, 2-methyl butanoic acid, and a combination thereof.

13. The method of claim 10, wherein contacting the organic waste with the alkali comprises contacting the organic waste with the alkali to form the intermediate compound, wherein the intermediate compound is a carbohydrate having one or more of the following functional groups: a hydroxyl group, a carboxyl group, a keto group, and an aldehyde group.

14. The method of claim 10, wherein contacting the organic waste with the alkali comprises contacting the organic waste with the alkali selected from the group consisting of an alkali metal compound, an alkali metal, an alkoxide, an alkali metal hydroxide, a carbonate, an alkali metal hydride, and a combination thereof.

15. The method of claim 10, wherein the contacting comprises heating the organic waste and the alkali to a temperature of about 150° C. to about 400° C. for about 10 seconds to about 5 minutes.

16. The method of claim 10, wherein the reducing further comprises adjusting the pH of a reaction mixture to about pH 2 to about pH 6.

17. The method of claim 10, wherein the reducing comprises heating the intermediate compounds and a metal catalyst mixture to a temperature of about 150° C. to about 400° C. for about 30 seconds to about 10 hours, wherein the metal catalyst mixture comprises a mixture of metal having high oxidation potential and copper.

18. The method of claim 10, wherein the method is performed in a batch reactor or a continuous flow reactor.

19. The method of claim 1, wherein the metal catalyst is a mixture of a metal having high oxidation potential and copper.

20. The method of claim 1, wherein the metal catalyst is a mixture of aluminum and copper.

21. The method of claim 10, wherein the metal catalyst is a mixture of a metal having high oxidation potential and copper.

22. The method of claim 10, wherein the metal catalyst is a mixture of aluminum and copper.

* * * * *